United States Patent [19]
Squirrell et al.

[11] Patent Number: 5,837,465
[45] Date of Patent: Nov. 17, 1998

[54] LUCIFERASE LABELLING METHOD

[75] Inventors: David James Squirrell; Melanie Jane Murphy, both of Porton Down, United Kingdom

[73] Assignee: The Secretary of State for Defence in Her Britannic Majesty's Government of the United Kingdom of Great Britian and Northern Ireland of Defence Evaluation & Research Agency, United Kingdom

[21] Appl. No.: 793,504

[22] PCT Filed: Aug. 30, 1995

[86] PCT No.: PCT/GB95/02038

§ 371 Date: Feb. 28, 1997

§ 102(e) Date: Feb. 28, 1997

[87] PCT Pub. No.: WO96/07100

PCT Pub. Date: Mar. 7, 1996

[30] Foreign Application Priority Data

Sep. 1, 1994 [GB]  United Kingdom ............... 9417593

[51] Int. Cl.$^6$ ............................... C12Q 1/68; C12Q 1/66
[52] U.S. Cl. ................. 435/6; 435/4; 435/8; 435/7.92; 435/7.93; 435/7.94; 435/7.95; 436/501; 436/547; 436/548; 530/391.3
[58] Field of Search ............................ 435/4, 7.1, 7.92, 435/8, 188, 6, 7.93, 7.94, 7.95; 436/501, 536, 543, 544, 547, 548; 530/391.3

[56] References Cited

U.S. PATENT DOCUMENTS 5,583,024  12/1996  McElroy et al. .................. 135/189

OTHER PUBLICATIONS

Analytical Biochemistry, vol. 175, No. 1, –1988 New York, NY U.S.A., pp. 14–21, XP 000563627, L.J. Kricka, "Clinical and biochemical applications of luciferase and luciferins".
Wannlund et al., Meth. Enzymol. 92:426–432, 1983.
Harlow et al., *Antibodies:A Laboratory Manual*, Cold Spring Harbor, 1988, pp. 553–558.
Clin. Chem. 40/3 347–357 (1994) Kricka Selected Strategies for Improving Sensitivity and reliability of Immunoassays.
Clin. Chem. 37/9, 1472–1481 (1991) Kricka "Chemiluminescent and Bioluminescent Techniques".
Bioluminescence and Chemiluminescence Fundamentals and Applied Aspects pp. 171–178 Kricka "The Clinical and Research Potential of Bioluminescence and Chemiluminescence in Medicine".
Series C: Mathematical and Physical Sciences vol. 226 pp. 237–248 Analytical Uses of Immobilized biological Compounds for Detection, Medical and Industrial Uses Coulet et al "Immobilized Biological Compounds in Bio–and Chemiluminescence Assays".

*Primary Examiner*—Robert D. Budens
*Attorney, Agent, or Firm*—Nixon & Vanderhye

[57] ABSTRACT

Luciferase is conjugated to a chemical entity, particularly to a specific binding agent such as an antibody, antigen or a nucleic acid, and more particularly an antibody, by (a) mixing the luciferase with one or more of D-luciferin, magnesium ions and adenosine triphosphate and (b) performing a covalent coupling reaction between the luciferase and the binding reagent using a covalent coupling reagent where the amount of D-luciferin, magnesium ions and/or adenosine triphosphate is sufficient to protect the luciferase activity against inhibition by the covalent coupling reagent. Preferably, step (a) is carried out by mixing the luciferase with its substrates in solution and preferably both magnesium and adenosine triphosphate are present as magnesium adenosine triphosphate ($Mg^{2+}$ ATP), optionally together with D-luciferin. Also disclosed is a labeled chemical entity comprising a chemical entity conjugated to active luciferase as formed by the method. Preferably, the chemical entity is a specific binding agent suitable for use in a specific binding assay, preferably being an antibody, antigen or nucleic acid. When the binding agent is a nucleic acid, it is preferably an oligonucleotide, but may be a polynucleotide or a nucleoside, and may be used as a hybridization probe or a chain extension primer, e.g., a PCR primer. The entity is an antibody as previous attempts to couple antibodies to luciferase have resulted in inactivity. Test kits are further provided.

24 Claims, 1 Drawing Sheet

LUCIFERASE LABELLING METHOD

This is a 35 U.S.C. 371 of PCT/GB95/02038, filed Aug. 30, 1995.

The resent invention relates to a method of labelling chemical materials, particularly biological materials, for the purpose of chemical, and particularly biological assay, and more particularly specific binding assay, such as immunoassay and hybridisation probing techniques and for incorporation of labels into specific amplification products e.g. using PCR in assay formats.

BACKGROUND OF THE INVENTION

The firefly luciferase mediated cleavage of luciferin (Eqn 1) has a high quantum yield and stable light output allowing the enzyme itself to be detected at very low concentrations using relatively simple instruments (see McCapra. Potential applications of bioluminescence and chemiluminescence in Turner et al (Edit.) Biosensors: fundamentals and applications: Oxford University Press, (1988): 617–37). Many methods have been developed using luciferase as an indirect label (see Wannlund and DeLuca, 'Bioluminescence immunoassays: Use of luciferase antigen conjugates for determination of methoxylate and DNP' in Deluca and McElroy (Edits). Bioluminescence and Chemiluminescence: Basic chemistry and analytical applications. London: Academic Press, (1981): 693–696; Geiger and Miska, Bioluminescence enhanced enzyme immunoassay: New ultrasensitive detection system for enzyme immunoassay, Clin. Chem. Clin. Biochem. J. (1987) 25. 31–38 and Murakami et al, Development of a bioluminescent detection system using adenylate kinase and firefly luciferase in Szalay et al (Edits.) Bioluminescence and chemiluminescence: Status Report, Chichester: John Wiley and Sons, (1993) 296–300.

The present inventors have noted that assay design could be much simplified whilst maintaining sensitivity by using luciferase as a direct label, but that methods of coupling it to assay binding agents are required that do not result in inactivation of what is well known to be a very labile enzymatic activity. The standard covalent coupling reagents such as glutaraldehyde, SMCC and SMPB rapidly and irreversibly inhibit luciferase activity.

Luciferase, eg that from *Photinus pyralis,* contains four cysteine residues (see de Wet et al (1987) Molecular and Cellular Biology) 7, 725–737 two of which are near to or part of the active site (see Deluca and McElroy (1978) Methods in Enzymology, 57, 3–15. The present inventors have determined that binding of covalent coupling reagents to these residues may cause the observed inactivation and have provided a method for coupling luciferase to assay agents that protects the enzyme from irreversible inhibition.

DESCRIPTION OF THE INVENTION

Figure 1:
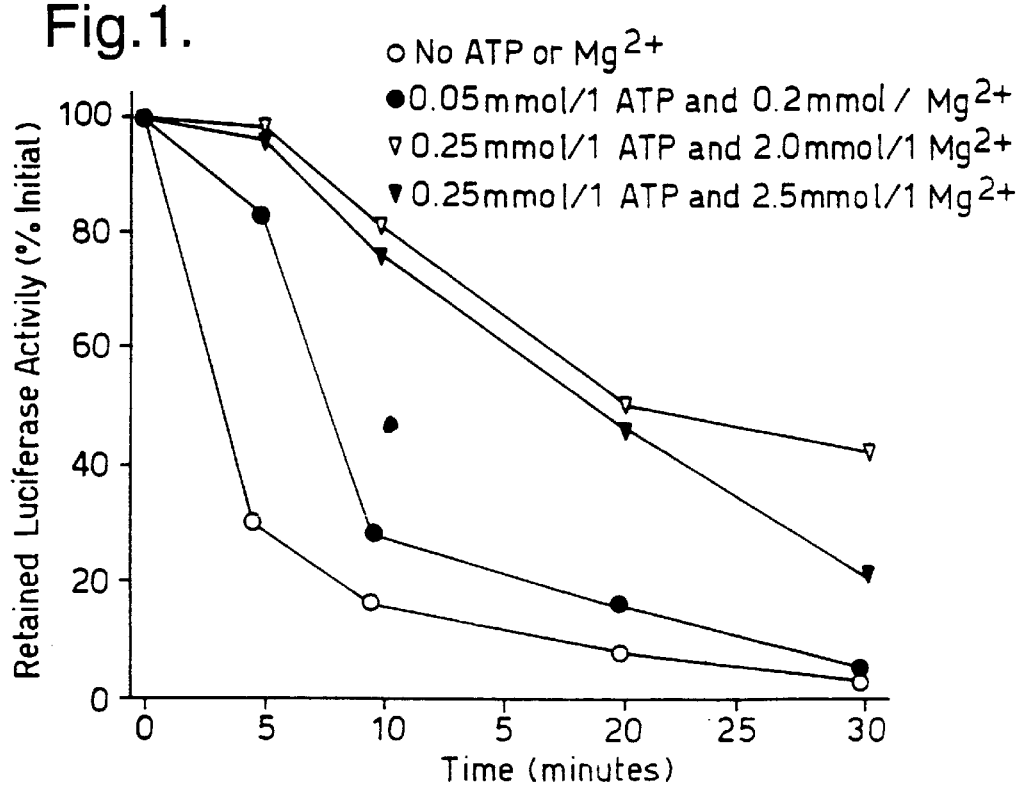
FIG. 1 is a plot of luminescence v. time as described in Example 1.

Thus in a first aspect of the present invention there is provided a method for conjugating firefly luciferase to a chemical entity, particularly to a specific binding agent such as an antibody, antigen or a nucleic acid, and more particularly an antibody, comprising (a) mixing the luciferase with one or more of D-luciferin, magnesium ions and adenosine triphosphate, such that the concentrations of magnesium ions and adenosine triphosphate are greater than 0.2 mmol/l and 0.05 mmol/l respectively and (b) performing a covalent coupling reaction between the luciferase and the chemical entity using a covalent coupling reagent.

Preferably the step (a) is carried out by mixing the luciferase with its substrates in solution and preferably both magnesium and adenosine triphosphate are present as magnesium adenosine triphosphate ($Mg^{2+}$ ATP), optionally together with D-luciferin. Preferably only one of $Mg^{2+}$ ATP or D-luciferin is present. If all three of $Mg^{2+}$, ATP and luciferin are present then it is preferable to exclude oxygen from the reaction mixture.

In a second aspect of the present invention there is provided a labelled chemical entity comprising a chemical entity conjugated to active firefly luciferase as provided by the method of the present invention. Preferably the chemical entity is a specific binding agent suitable for use in a specific binding assay, preferably being an antibody, antigen or nucleic acid. When the binding agent is a nucleic acid it is preferably an oligonucleotide, but may be a polynucleotide or a nucleoside, and may be used as a hybridisation probe or a chain extension primer, eg a PCR primer. Most advantageously the entity is an antibody as previous attempts to couple antibodies to luciferase have resulted in almost complete inactivity.

A particular advantage of provision of luciferase labelled chemical entities, and particularly luciferase labelled antibodies, is the enablement of performance of light guide associated capture assays. In one preferred such assay a capture antibody for a target antigen is immobilised upon a lightguide such as an optic fibre that is arranged to input light falling upon it to a light measuring device eg a photomultiplier; an antigen to be measured is applied to the lightguide in a liquid sample and a second antibody, characterised in that it is labelled with luciferase, is contacted in solution with the lightguide whereupon it becomes bound to the already captured antigen that has been bound to the capture antibody.

In order to determine the presence and/or amount of the captured antigen it is only necessary to contact D-luciferin and $Mg^{2+}$ ATP in solution with the surface of the lightguide, which has the antigen-antibody complex bound to it, and to measure the amount of light emitted and transferred to the light measuring device eg photomultiplier. In this manner it is possible for luminometric assays of greater sensitivity to be carried out, with multiple specificity provided by use of several lightguides each capable of capturing a different antigen and placed in a single sample chamber such that several different immunoassays can be carried out simultaneously by adding several different luciferase labelled antibodies in the same step.

Alternatively a charge couple device (CCD) or equivalent such as diode arrays or photomultipliers might be used to monitor a number of discrete areas on a 1 or 2 dimensional detector array surface simultaneously, each with a different immobilised antibody specific for a different antigen, such that presence of a particular antigen might be detected by the position of light emission. Similarly, use of such lightguides or charge couple devices onto which antigens or anti-immunoglobulin antibodies specific for a target antibody have been immobilised allows competition binding assays for specific antibodies wherein the amount of luciferase labelled antibody bound to the antigen on the lightguide will be reduced when competing antibody is added at the same time in the form of a sample.

On removal of the sample and luciferase labelled antibody and exposure of the lightguide to D-luciferin and $Mg^{2+}$ ATP substrate solution the amount of light detected at the photomultiplier may be related to the amount of antibody in the sample that is specific for the immobilised antigen or anti-immunoglobulin antibody.

It will be realised that if lightguides having oligonucleotide probes bound to their surfaces (see method in applicant's WO 9306241) and oligonucleotides labelled with luciferase are employed that assay of oligonucleotides and polynucleotides will be possible in analogous manner to the antibody-antigen assays described above. Furthermore, using different lightguides or array areas, simultaneous assay of antigens and nucleic acids will be possible from a single sample.

A particular advantage of performing luciferase labelled binding assays on the surface of a light guide such as a planar waveguide or an optic fibre (these may be multiplexed) is that the need to separate reagents from the species of interest, ie the bound species, is reduced as light generated within a few hundred nanometers of the lightguide surface, is preferentially detected by the detector while light generated in bulk solution is not. Thus assays using such format (usually termed evanescence) would require no wash steps or sequential additions of reagents, and thus could be carried out very quickly and optionally in a flow of liquid using a flow cell.

The labelled agents of the present invention, the method for producing them and a method for their use will now be exemplified by way of illustration only by reference to the following non-limiting Examples and Figures.

FIGURES

FIG. 1 shows a plot of luminescence v time obtained after incubation of luciferase with covalent coupling reagent with protection by varying quantities of $Mg^{2+}$ ATP as described in Example 1.

Figure 2:
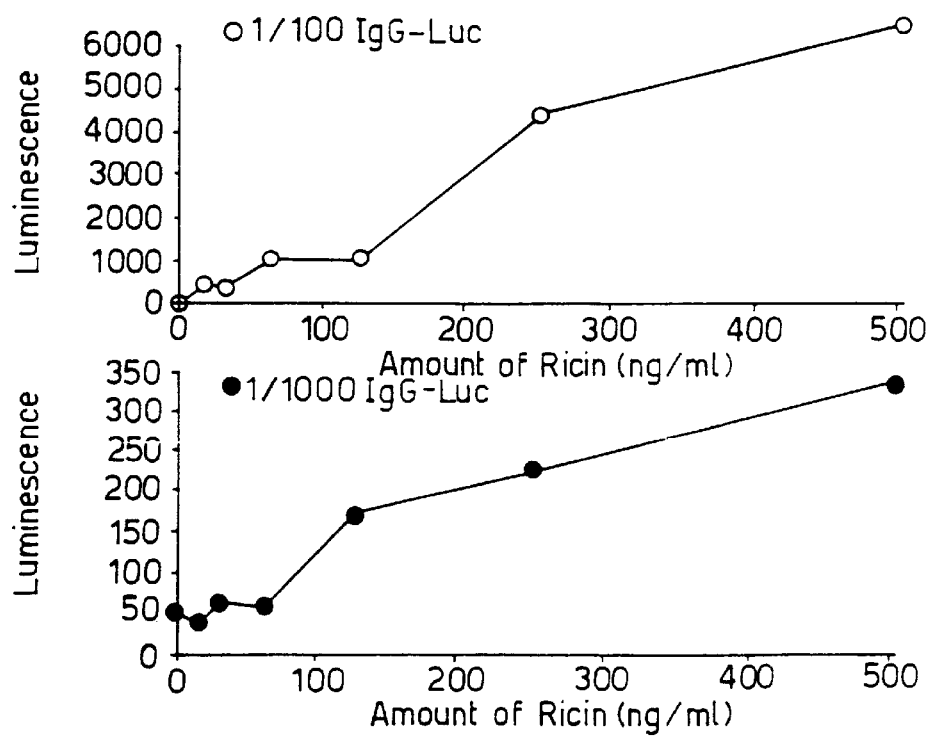
FIG. 2 is a plot of luminescence v. amount of ricin as described in Example 1.

FIG. 2 shows a plot of luminescence v amount of ricin for an assay as carried out as described in Example 1. The upper plot is that obtained using a 1/100 dilution of the IgG-luciferase conjugate while the lower plot uses a 1/1000 dilution.

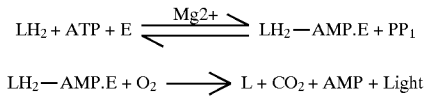

Eqn 1: The Firefly Luciferase Reaction $$LH_2 + ATP + E \xrightleftharpoons{Mg^{2+}} LH_2-AMP.E + PP_1$$

$$LH_2-AMP.E + O_2 \longrightarrow L + CO_2 + AMP + Light$$

where $LH_2$ is luciferin, E is luciferase, AMP is adenosine monophosphate, $PP_1$ is inorganic pyrophosphate, and L is oxyluciferin.

EXAMPLE 1

A Multilite® Luminometer and 3.5 ml polystyrene tubes (Biotrace Bridgend UK) were used for all light measurements. Firefly luciferase (L-5256), DTT, BSA (Fraction V), ATP and ricin were obtained from Sigma (Poole, UK); D-luciferin was obtained from Fluka (Gillingham, UK) and sulphosuccinamidyl-4-(N-maleimidomethyl)cyclohexane-1-carboxylate (sulfo-SMCC) was obtained from Pierce and Warriner (Chester, UK). Sheep-anti-ricin antibodies were produced by conventional techniques and other reagents were of analytical grade.

Luciferase substrate was 10 mmol/liter HEPES buffer pH7.75 containing 0.4 mmol/liter D-luciferin, 40 mmol/liter magnesium sulphate, 2 mmol/liter. ATP, 2 mmol/liter EDTA, 2 mmol/liter DTT, 0.2% BSA and 2 gmol/liter sodium pyrophosphate. Substrate was prepared fresh daily from stock solutions. The Luciferase activity assay was carried out by adding $2\times10^{-6}$l of the sample to be assessed to $200\times10^{-6}$l of substrate (described above) in a 3.5 ml polystyrene tube and luminescence was measured after a 5 second delay, integrated over a 10 second period.

Substrate protection method: Luciferase at 4.2 gmol/liter was mixed with sulfo-SMCC at 630 gmol/liter in 10 mmol/liter HEPES buffer at pH 7.75, and the mixture incubated at room temperature for 30 minutes. At timed intervals a sample was removed from the reaction mixture and diluted 100-fold in buffer and the luciferase activity of the sample measured. Various concentrations of $Mg^{2+}$ ATP or D-luciferin were added to the mixture and their effect on activity monitored to determine the most effective protection against inhibition.

Covalent coupling with sulfo-SMCC: sheep IgG raised against ricin was reduced to release thiol groups by reaction with 2-mercaptoethylamine-HCl at 37° C. for 90 minutes (see Pierce Warriner kit instructions). 4 mg luciferase was prepared in 1 ml phosphate buffer pH 7.0 containing 0.5 mmol/liter ATP and 2.5 mmol/liter magnesium sulphate. 50 μl of 20 mmol/liter sulfo-SMCC in phosphate buffer pH 6.0 was added and the mixture incubated at room temperature for 30 minutes. The activated luciferase was purified using a Pierce GF-5 desalting column and activated luciferase and reduced IgG were combined at a molar ratio of 1:1 in phosphate buffer pH 7.0 containing 0.25 mmol/liter EDTA, 0.5 mmol/liter ATP and 2.5 mmol/liter magnesium sulphate. The reaction was allowed to proceed at room temperature for 30 minutes and then stopped by adding 10 μl 1 mol/liter cysteine for 20 minutes before purifying the luciferase-antibody conjugate on a Pierce GF-5 desalting column. The product was stored at 4° C. in sodium phosphate buffer pH 7.0 containing 0.25 mmol/liter EDTA until required.

The activity remaining in the conjugated luciferase was assessed by performance of an ELISA assay as set out below:

Tube-based bioluminescent ELISA: Polystyrene tubes were coated with 100 μl ricin in carbonate-bicarbonate buffer pH 9.6 containing 0.02% thiomersal overnight at 4° C. The luciferase-antibody conjugate was diluted in phosphate buffered saline (PBS) and after blocking of tubes with 200 μl 1% BSA, 100 μl labelled antibody was added and incubation carried out for 1 hour at 37° C. The tubes were washed five time in PBS containing 5% Tween 20® (polyoxyethylene (20) Sorbitan monolaurate) 200 μl substrate was added to each tube and luminescence measured immediately.

Results: The results obtained from substrate protection by $Mg^{2+}$ ATP are shown in FIG. 1 where % remaining activity as indicated by luminometer readings is plotted against time as derived by removal of samples (3 repeats each point) from the reaction mixture which contained $0.63\times10^{-6}$ mol/liter sulfo-SMCC, $4.2\times10^{-6}$ mol/liter luciferase and $Mg^{2+}$ ATP. Plots are shown for reaction with no $Mg^{2+}$ or ATP; 0.03 mmol/liter ATP and 0.2 mmol/liter $Mg^{2+}$, 0.25 mmol/liter ATP and 2.0 mmol/liter $Mg^{2+}$, 0.25 mmol/liter ATP and 2.5 mmol/liter $Mg^{2+}$. D-luciferin was also assessed for protective effect (not shown) and was found to give some retention of activity but significantly less than that of $Mg^{2+}$ ATP. The maximum D-luciferin concentration tested was 1 mmol/liter and allowed retention of 11% of initial luciferase activity after 30 minutes exposure to sulfo-SMCC as compared to over 40% using the $Mg^{2+}$ ATP.

Tube based bioluminescent ELISA results are shown in FIG. 2. The polystyrene tubes were used to allow light measurements to be made directly in the Multilite® luminometer but microtitre plates and a plate luminometer could equally be used. The results show that an active luciferase-antibody conjugate is produced and that the antibody retains its binding properties.

EXAMPLE 2

A sheep polyclonal antibody raised to ricin was covalently coupled to an optic fibre connected to a photomultiplier tube; the section of the fibre with antibody coupled to it residing within a chamber capable of being filled with a variety of solutions and emptied as required. The assay followed the following cycle:

(i) D-luciferin containing substrate solution added to the chamber such that any luciferase present would cause light to be emitted;

(ii) substrate solution replaced by test sample including ricin;

(iii) test sample solution replaced with solution containing sheep anti-ricin IgG labelled with luciferase;

(iv) sheep anti-ricin solution replaced with D-luciferin containing substrate solution;

(v) substrate solution replaced by regeneration buffer.

Using this format it is possible to determine the amount of ricin in the test sample by relating the increase in signal from the photomultiplier tube during the step (iv) over the prior signal and relate that to the amount of ricin, eg using a standard curve obtained using signal increase for known amounts of ricin.

The method for conjugating luciferase and the labelled chemical entities described in this application may also be suitable for the luciferases described in WO 9525798. Similarly the method may also be suitable for other luciferases.

We claim:

1. A method for conjugating firefly luciferase to an antibody or nucleic acid, comprising the steps of:
   (a) mixing firefly luciferase with a reagent selected from the group consisting of (i) D-luciferin, (ii) magnesium ions and adenosine triphosphate (ATP), and (iii) D-luciferin, magnesium ions and adenosine triphosphate, such that the concentrations of magnesium ions and adenosine triphosphate, when present, are greater than 0.2 mmol/liter and 0.05 mmol/liter, respectively; and
   (b) covalently coupling the luciferase and the antibody or nucleic acid using a covalent coupling agent; with the proviso that if reagent (iii) is used, then oxygen is excluded from the reaction.

2. A method as claimed in claim 1 wherein step (a) is carried out by mixing the luciferase with any of reagents (i), (ii) or (iii) in solution.

3. A method as claimed in claim 1 wherein in (ii) or (iii) the magnesium ions and adenosine triphosphate are present as magnesium adenosine triphosphate ($Mg^{2+}$ ATP).

4. A method as claimed in claim 1 wherein step (a) is performed using at least 0.2 mmol/liter ATP for $4 \times 10^{-6}$ mol/liter luciferase.

5. A method as claimed in claim 4 wherein step (a) is performed in the presence of 2 mmol/liter magnesium ions.

6. A method as claimed in claim 1 wherein the covalent coupling reagent comprises glutaraldehyde, succinimidyl-4-(N-meleimidomethyl)-cyclohexane-1-carboxylate (SMCC) or succinimidyl-4-(p-maleimidophenyl) butyrate (SMPPB).

7. A method as claimed in claim 1 wherein step (b) is performed with the covalent coupling reagent after the luciferase has been mixed with reagents (i), (ii) or (iii).

8. A method as claimed in claim 7 wherein 0.5 mmol/liter ATP is used.

9. A method as claimed in claim 1 wherein the antibody or nucleic acid is a specific binding agent suitable for use in a specific binding assay.

10. A method as claimed in claim 9 wherein the specific binding agent is an antibody.

11. A method for conjugating firefly luciferase to a chemical entity, comprising the steps of:
    (a) mixing firefly luciferase with magnesium ions and adenosine triphosphate, such that the concentrations of magnesium ions and adenosine triphosphate are greater than 0.2 mmol/liter and 0.05 mmol/liter, respectively; and
    (b) covalently coupling the luciferase and the chemical entity using a covalent coupling reagent.

12. A method for conjugating firefly luciferase to a chemical entity comprising the steps of:
    (a) mixing firefly luciferase with D-luciferin, magnesium ions and adenosine triphosphate, such that the concentrations of magnesium ions and adenosine triphosphate are greater than 0.2 mmol/liter and 0.05 mmol/liter, respectively; and
    (b) covalently coupling the luciferase and the chemical entity using a covalent coupling reagent; with the proviso that oxygen is excluded from the reaction.

13. A specific binding assay which uses a labelled antibody or nucleic acid as claimed in claim 10.

14. A specific binding assay as claimed in claim 13 wherein the presence or amount of a target chemical entity is determined by specifically binding it to an antibody or nucleic acid conjugated to active luciferase, exposing the bound entity to D-luciferin under conditions wherein luciferase will cleave the D-luciferin and cause light to be emitted, and relating the amount of any light emitted to the presence or amount of the target chemical entity.

15. A specific binding assay as claimed in claim 13 wherein the target chemical entity is an antigen and is captured by a capture antibody specific for it before binding to the antibody or nucleic acid conjugated to active luciferase.

16. A specific binding assay as claimed in claim 15 wherein the antibody conjugated to active luciferase is an antibody specific to the target antigen.

17. A specific binding assay as claimed in claim 15 wherein the capture antibody is conjugated to a light-guide which feeds light to a light measuring device.

18. A specific binding assay as claimed in claim 17 wherein the light guide is an optic fiber.

19. A specific binding assay as claimed in claim 15 wherein a light detector device is used to monitor a number of discrete areas on a 1 or 2 dimensional detector array surface simultaneously, each area having a different immobilized antibody or antigen specific for a different antigen or antibody, respectively, such that presence of a particular antigen is detected by the position of detected light emission.

20. An assay as claimed in claim 19 wherein the light detector device is a charge couple device.

21. An antibody or nucleic acid conjugated to active luciferase according to the method of claim 1.

22. A test kit comprising an antibody or a nucleic acid conjugated to active luciferase by the method of claim 1.

23. A test kit as claimed in claim 22 wherein the conjugated luciferase has 10% or more of the activity of the luciferase from which the labelled antibody was prepared.

24. A test kit as claimed in claim 22 which comprises a light guide or light detector array onto which antibodies, antigens or nucleic acids have been immobilized.

* * * * *

Disclaimer

5,837,465—David James Squirrell; Melanie Jane Murphy, both of Porton Down, United Kingdom. LUCIFERASE LABELLING METHOD. Patent Dated November 17, 1998. Disclaimer filed on June 22, 2005, by Assignee, THE SECRETARY OF STATE FOR DEFENCE IN HER BRITANNIC MAJESTYS' GOVERNMENT OF THE UNITED KINGDOM OF GREAT BRITAIN AND NORTHERN IRELAND.

Hereby enters this disclaimer to claim 11, of said patent.

*(Official Gazette, September 20, 2005)*